United States Patent [19]

Colas et al.

[11] Patent Number: 5,232,935

[45] Date of Patent: Aug. 3, 1993

[54] COMPOSITION FOR ENHANCING DRUG PERMEATION

[75] Inventors: André L. R. Colas, Glashuetten, Fed. Rep. of Germany; Jonathan Hadgraft, Penarth, Wales; Vivien L. C. Moffat, Elst, Netherlands; Franck A. D. Renauld, Overijse, Belgium

[73] Assignee: Dow Corning France S.A., Valbonne, France

[21] Appl. No.: 904,743

[22] Filed: Jun. 26, 1992

[30] Foreign Application Priority Data

Jul. 3, 1991 [GB] United Kingdom ............... 9114346

[51] Int. Cl.$^5$ .................. A61K 31/44; A61K 31/415
[52] U.S. Cl. .................... 514/356; 514/63; 514/398; 514/772; 514/947
[58] Field of Search ............... 514/356, 398, 947

[56] References Cited

U.S. PATENT DOCUMENTS 5,021,405  6/1991  Klimisch ..................... 514/63

FOREIGN PATENT DOCUMENTS 58-127214  of 1983  Japan.
2223232  4/1990  United Kingdom.

OTHER PUBLICATIONS

Chemical Abstracts 101:157725s (1984).
Chemical Abstracts 110:28918u (1989).

Primary Examiner—Leonard Schenkman
Attorney, Agent, or Firm—John L. Chiatalas

[57] ABSTRACT

A method of accelerating the permeation of drugs in topical and transdermal delivery of a drug in which a drug is applied to the skin in combination with organosilicon compounds which are carboxyalkyl functional polysiloxanes and alkylsulphoxide functional polysiloxanes. The organosilicon compound may be applied to the skin neat or in the form of a solvent solution containing the organosilicon compound.

21 Claims, No Drawings

COMPOSITION FOR ENHANCING DRUG PERMEATION

This invention is concerned with the enhancement of the permeation of drugs through the skin of the human or animal body by use of certain organosilicon compounds.

Various techniques are known for the topical application of medicines and drugs to the skin of the human or animal body including the application of ointments and the so-called transdermal delivery techniques in which patches are adhered to the body. The skin tends to resist penetration into the body of drugs applied topically. When the drug contacts the skin the rate of permeation of the drug through the skin is related to hydrophobicity. Many organic materials have been proposed to accelerate this process and are referred to as skin penetration enhancers for example oleic acid and decylmethylsulphoxide. However, many of these induce unacceptable skin irritation.

Japanese Kokai Patent 58-12102 (Nitto Denki Kogyo KK) published Jul. 30, 1983 discloses a base composition for enhancing the penetration of medicines through skin comprising a lower alcohol and one or more cyclic or linear polydimethylsiloxanes of extremely low viscosity. The polydimethylsiloxanes disclosed have no functional organic groups.

We have now found that an improved skin penetration enhancement may be achieved by use of certain carboxyalkyl functional polysiloxanes and alkylsulphoxide functional polysiloxanes.

The present invention provides in one of its aspects a composition for use in the delivery of a drug to the human or animal body via the skin comprising an organosilicon compound selected from the group consisting of polysiloxanes having silicon-bonded carboxyalkyl or alkylsulphoxide groups.

In a composition according to the present invention, the organosilicon compound preferably has the average general formula $R'_a R_{3-a} SiO[R_2 SiO]_m [R'RSiO]_x SiR'_a R_{3-a}$ in which at least one R' represents a carboxyalkyl group —(CH$_2$)$_y$COOH or an alkylsulphoxide group —(CH$_2$)$_z$SOR and the remainder are groups R, R represents a monovalent hydrocarbon group having from 1 to 6 carbon atoms, the groups R being at least predominantly methyl, a has a value of 1, y is an integer having a value of one to thirty; z is an integer having a value of one to ten and m and x have values (e.g. up to 1000) such that the organosilicon compound is a liquid at room temperature. In preferred materials m and x have values from 0 to about 10, more preferably 0 to 5.

Suitable polysiloxanes having silicon-bonded carboxyalkyl or alkylsulphoxide groups for use in the present invention include those of the following structural formulae:

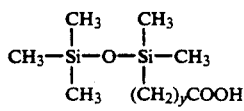

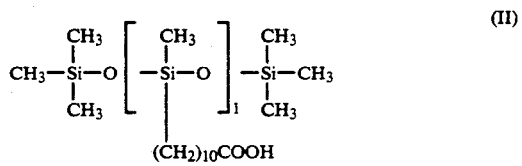

and

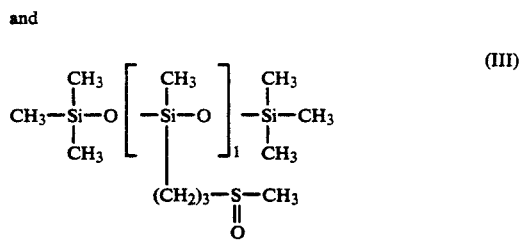

in which x is an integer having a value of one to about one thousand; y is an integer having a value of one to about thirty; z is an integer having a value of one to ten and R is an alkyl group having from one to six carbon atoms. Preferred materials are those having a comparatively low molecular weight.

Some specific examples of these compounds are:

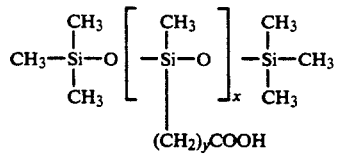 (I)

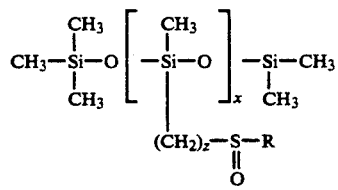 (II)

and

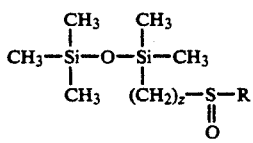 (III)

In the following examples and in the tables these materials are referred to by the Roman numerals indicated above. For example, the alkylsulphoxide functional polysiloxane (III) will be referred to hereinafter as Compound (III).

These carboxyalkyl and alkylsulphoxide functional polysiloxane compounds may be prepared by methods well known in the art. Thus, the alkylcarboxy substituted polysiloxanes (I) and (II) may be prepared by hydrosilylation of undecylenic silyl ester with the corresponding polysiloxane having a silicon-bonded hydrogen atom, followed by methanolysis and the alkylsulphoxide substituted polysiloxane (III) may be prepared by oxidation of the corresponding alkylsulphide substituted polysiloxane as more fully described in G.B. 2 223 232A.

The organosilicon compounds may be employed as drug permeation enhancers by applying them to the skin neat or in admixture with a solvent. The skin can be pretreated with the organosilicon enhancer compounds prior to the application of the drug, or the organosilicon enhancer compounds may be formulated as medicinal ingredients and applied to the skin in conjunction with the drug.

Thus, a composition according to the invention may comprise the polysiloxane alone or in admixture with a solvent for the polysiloxane. Ethanol is the preferred solvent, but other short chain alcohols may be employed such as isopropanol and isobutanol. Preferred compositions may comprise sufficient alcohol to provide a solvent solution containing up to 30% or more of the polysiloxane.

A composition according to the invention may also comprise a hydrophobic or hydrophilic drug or excipient selected according to the usual pharmaceutical practices for topical drug application.

The advantages of this invention are that quite unexpectedly it has been found that drug permeation through the human skin can be accelerated when the drug is applied in conjunction with the polysiloxanes having silicon-bonded carboxyalkyl or sulphoxide substituents as referred to above. In particular, this advantage is achieved when the composition according to the present invention comprises a lower aliphatic alcohol and the polysiloxane in proportions such that the composition comprises from three to thirty percent by weight polysiloxane. Preferred compositions of this invention do not cause an unacceptable level of skin irritation often inherent with the prior art organic enhancers. This is advantageous in the case of subjects having sensitive skin.

The invention is applicable in the treatment of human and animal bodies and may be especially useful for the manufacture of a medicament for accelerating the permeation of drugs in topical and transdermal delivery of drugs. Thus, the compositions of this invention may be used in patch, ointment, salve and lotion forms containing drugs.

Drugs whose penetration through the human skin have been shown to be enhanced by a composition according to the present invention include the Model drugs metronidazole and methyl nicotinate although the invention is applicable to any hydrophobic or hydrophilic drug.

The invention also relates to a method of accelerating the permeation through the skin of the human or animal body of drugs applied thereto. In carrying out such a method, a composition according to the invention may be applied to the skin. As stated above the composition comprises a selected polysiloxane with or without a solvent and with or without a drug. Thus, the organosilicon compound may be applied neat to the skin or it may also be employed in the form of a solvent solution. The organosilicon compound can be applied to the skin prior to, and independently of, the application of the drug to the skin.

These and other features, objects and advantages of the present invention will become more apparent from a consideration of the following detailed description thereof.

The skin irritancy potential of compositions was assessed using the mouse ear irritancy assay reported by Evans, F. J. and Schmidt, R. J. (1979), entitled "An Irritancy Procedure for the Comparative Irritancy Testing of Esters in the Tigliane and Daphnane Series", Inflammation, 3, pages 215 to 223. In addition to compositions according to the present invention there were included in the testing protocol oleic, acid referred to hereinafter as OA, undecanoic acid, referred to hereinafter as UA and decylmethylsulphoxide, referred to hereinafter as DEMSO. Polysiloxane (I) was prepared according to the scheme

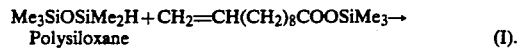

Me$_3$SiOSiMe$_2$H + CH$_2$=CH(CH$_2$)$_8$COOSiMe$_3$→ Polysiloxane (I).

The pentamethyldisiloxane was prepared by equilibration of an excess of hexamethyldisiloxane (3 moles) and tetramethyldisiloxane (1 mole) in presence of 0.1% of trifluoroacetic acid at 70° C. for 4 hours. Distillation after neutralisation gave the pentamethyldisiloxane with 50% of hexamethyldisiloxane. The pentamethyldisiloxane was used as such taking into account the nonreactivity of the hexamethyldisiloxane in hydrosilylation. 0.2 mole of undecylenic acid silylester was heated to 108° C. in presence of H$_2$PtCl$_6$ as catalyst and sufficient of the pentamethyldisiloxane was added to give the corresponding undecylenic silyl ester pentamethyldisiloxane. Methanolysis at room temperature yielded the polysiloxane (I).

Polysiloxane (II) was prepared according to the scheme (Me$_3$SiO)$_2$SiMeH + CH$_2$=CH—(CH$_2$)$_8$COOSiMe$_3$→Polysiloxane (II).

0.33 mole undecylenic silyl ester was heated to 108° C. in presence of H$_2$PtCl$_6$ as catalyst and 0.33 mole of heptamethyl trisiloxane was added. After the reaction was complete the product was cooled and distilled. The undecylenic silyl heptamethyl trisiloxane was treated with methanol at room temperature to product polysiloxane (II).

Polysiloxane (III) was prepared according to the scheme

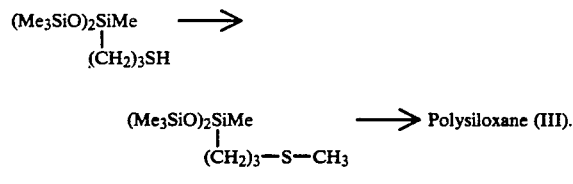

(Me$_3$SiO)$_2$SiMe
|
(CH$_2$)$_3$SH (Me$_3$SiO)$_2$SiMe                    ⟶ Polysiloxane (III).
|
(CH$_2$)$_3$—S—CH$_3$ To a solution of 0.2 mole of mercapto propyl heptamethyltrisiloxane and 59 g of methanol, 0.21 mole of sodium hydroxide in 20 g of water were slowly added and the flask temperature maintained at 15° to 20° C. with an ice/water bath. 0.22 mole of iodo methane were slowly added. The solution was stirred for 15 minutes at room temperature and 20 g of water were added. The organic phase was then separated, dried and distilled to give the sulphide functional heptamethyltrisiloxane. 0.15 mole of the methyl propyl sulphide heptamethyltrisiloxane in 12 g methanol, 30 g isopropanol and 200 mg of Adogen 464 as phase transfer catalyst were added to 0.16 mole of sodium periodate and 100 g of H$_2$O. The mixture was kept at 20° C. with a water bath for 20 hours and then extracted with carbon tetrachloride. The organic phase was treated with 1 g of sodium bisulphite, dried and distilled to give the corresponding sulphoxide.

An in vivo procedure involved the application of ethanolic solutions of each compound to the inside ear surface of female mice. A pilot assay was performed initially to determine the approximate range of irritant concentrations for each compound. In both the pilot assay and the main assay five different concentrations of each compound were tested. At specific time intervals the number of positive reactions in each group of mice was recorded as a quantal response.

From the results of the main assay, the dose of each test compound causing an irritant response in fifty percent of subjects (I.D. 50) was calculated by a probit method. This method enables comparison between the irritancy potential of each of the test compounds to be assessed. For each irritant concentration the time to maximum erythema was also recorded.

EXAMPLE I

Pilot Assay

Forty female white WSP mice weighing 24 to 30 g (average weight 25 g) were housed in groups of five per cage. Standard pelleted food and water was available ad libidum.

With the exception of UA and DeMSO the test compounds were liquids, and five ethanolic dilutions were prepared in the concentration range between a neat compound (100%) to 1% w/v. For UA the dilutions were prepared between 80% and 1% w/v and for DeMSO the concentrations were prepared in the range from 20% to 0.1% w/v.

One cage of mice was allocated to each compound and a ten microliter (10 µl) aliquot from one of the dilutions was applied to the inner surface of one ear of one mouse using a Microcap pipette. The untreated ear of each mouse served as a negative control. This procedure was repeated for the remaining four dilutions of the test compound using the remaining mice in the cage, and one mouse was treated with each of the concentrations in the selected range for each test compound.

The mouse ears were examined at the following time intervals post-application: 15 minutes, 30 minutes, 1, 2, 4 and 24 hours. Each mouse ear was scored as either a positive or negative irritant response based on the presence or absence of erythema either between the ear capillaries or over the entire area of test application site. The time to maximum erythema was also noted.

From the results of the pilot assay five dilutions of each test compound were prepared for use in the main assay. The concentration range was narrowed and was selected to include only one dilution expected to give 100% irritant response.

EXAMPLE II

Main Assay

Fifty female white WSP mice, average weight 25 g, were housed in cages of ten. The animals were kept under the same conditions as Example I. Each group of ten was allocated to one of the five concentrations of each test compound.

The test procedure was conducted as in Example I and the total number of red ears per dilution was recorded at each time point. Mice were examined before and after the expected time to maximum erythema to confirm the time to peak response observed in the pilot assay. The I.D. 50 for each compound was calculated by probit analysis using a standard computer programme.

The results of the irritancy study are shown below in Table A.

TABLE A

| Test irritant | F. Wt | Time to peak irritancy | ID50 mg/10 µl | ID50 m mol/10 µl |
|---|---|---|---|---|
| Oleic Acid | 282.5 | 1 hour | 3.459 | .0122 |
| Undecanoic Acid | 186.3 | 1 hour | 0.986 | .0053 |
| I | 332 | 1 hour | 1.084 | .0033 |
| II | 406 | * | * | * |
| DeMSO | 204 | 30 min | 0.050 | .00025 |
| III | 326 | 30 min | 0.147 | .00046 |

*This compound was considered to be non-irritant as only 3 of the 50 subjects tested showed a transient positive response after 30 minutes to primary insult by two of the dilutions of II in ethanol. No reactions were observed when neat silicone was applied to the skin.

From the values of I.D. 50 (m moles) it can be seen that I is of the same order of irritancy as undecanoic acid and that II was considered to be non-irritant. III is slightly less irritant than the established organic skin penetration enhancer DeMSO.

EXAMPLE III

In vitro permeation studies were performed on full thickness human cadaver skin (abdominal) mounted in Franz type glass diffusion cells with the stratum corneum uppermost (surface area=0.196 cm$^2$, volume of receptor compartment =5.5 cm$^3$). Phosphate buffered saline pH 7.4 was used as the receptor phase. The cells were placed on a magnetic stirring table immersed in a water bath maintained at 37° C.

Prior to the start of each experiment, the untreated skin cells were equilibrated in the water bath for one hour. After this time, and periodically during the course of the experiment, any air bubbles which had accumulated in the receptor phase were removed by gentle inversion of the skin cell.

Samples from the same donor were treated either with 10 µl silicone enhancer or an ethanolic solution of silicone (3% or 30% w/v) two hours prior to the introduction of the model skin permeant metronidazole (MDZ) into the donor compartment. 35 µg MDZ was applied to the skin surface as a thin film to represent the finite dose technique (40 µl of an ethanolic solution MDZ 5 µmol/ml). Control skin samples were either left untreated or treated with 10 µl absolute ethanol. The upper surface of the skin in the donor compartment was left exposed to the atmosphere throughout the course of the experiment and a foil cover was placed over the sampling arm of each cell.

The flux of MDZ across the skin was measured over a 48 hour period. 0.5 ml samples were withdrawn from the receptor compartment at specified time intervals and replaced with an equal volume of pre-heated buffer solution to maintain a constant volume.

The samples were analysed for MDZ content by an HPLC technique and corrections were made for the progressive dilution of the receptor phase caused by successive sampling. The results were expressed as cumulative % dose permeated v time.

Experiments were performed to evaluate the effect of the following treatments on the flux of MDZ:
1. Compound (III) 3% and 30% in EtOH.
2. Compounds (I) and (II) 3% and 30% in EtOH and neat.
3. Oleic acid (OA) 30% in EtOH and Undecanoic acid (UA) 3% and 30% in EtOH.

The results were recorded as the enhancement factor (EF) which was calculated as shown below. The enhancement factor for the materials tested is shown in the accompanying Tables.

$$\text{Enhancement Factor } (E.F.) = \frac{\text{Ave \% Dose Permeated (treated)}}{\text{Ave \% Dose Permeated (control)}}$$

TABLE I

|  | II 3% | I 3% | UA 3% |
|---|---|---|---|
| E.F. 24 hours | 4.4 | 3.4 | 1.6 |
| E.F. 48 hours | 3.9 | 3.7 | 1.0 |

TABLE II

|  | II 30% | I 30% | UA 30% | OA 30% |
|---|---|---|---|---|
| E.F. 24 hours | 3.2 | 3.1 | 3.2 | 3.4 |
| E.F. 48 hours | 3.7 | 3.5 | 3.5 | 3.7 |

TABLE III

|  | II neat | I neat |
|---|---|---|
| E.F. 24 hours | 2.7 | 2.8 |
| E.F. 48 hours | 2.3 | 2.3 |

TABLE IV

|  | III 3% | III 30% |
|---|---|---|
| E.F. 24 hours | 3.4 | 2.8 |
| E.F. 48 hours | 4.5 | 3.2 |

A significant difference was observed between the permeation of MDZ through skin samples treated with 3% of the silicones when compared to control values.

EXAMPLE IV

In vitro permeation studies of methyl nicotinate (MN) were performed on full thickness human cadaver skin and the Franz type diffusion cells assembled as described in Example III.

50 μl aliquots of silicone enhancers I to III were applied as ethanolic solutions (30% w/v) to the skin surface two hours prior to the introduction of MN into the donor compartment (n=3 for each treatment). 0.3 ml 0.5M solution of MN in phosphate buffered saline was applied to the skin surface and the permeation of MN was measured over a 24 hour period. 0.5 ml samples were withdrawn from the receptor phase and the concentration of MN in each sample was determined by an HPLC technique.

From the slope of the cumulative amount permeated v time profile the permeability coefficient Kp was calculated:

Permeability Coefficient $(Kp) =$ $$\frac{\text{Flux } (J) \text{ mol hour}^-}{\text{Area } (A) \text{ cm}^2 \times CONCN (C) \text{ mol cm}^{-3}}$$

Experiments were performed to evaluate the effect of the following treatments on the flux of MN : 30% w/v solutions of Compounds I, II and III in EtOH.

Enhancement Ratio (E.R.) = Kp Treatment/Kp Control

TABLE V

|  | $Kp^1$ treated* | sd (n = 3) | Kp control | sd (n = 3) | E.R. |
|---|---|---|---|---|---|
| I 30% | 5.52 | 1.6 | 3.07 | 0.24 | 1.8 |
| II 30% | 14.9 | 0.7 | 3.72 | 1.2 | 4.0 |
| III 30% | 7.57 | 0.25 | 3.86 | — | 2.0 |

*Kp values are indicated as Kp × $10^{-3}$ cm hr$^{-1}$

A significant difference was observed between the permeation of MN through skin samples treated with the organosilicon compounds I to III when compared to control values.

With further regard to Example III no significant difference was observed between the permeation of MDZ through skin samples treated with three or thirty percent by weight of organosilicon compounds similar to the cyclic and linear polydimethylsiloxanes described in the Japanese Kokai Patent 58-128324 when compared to control values.

With further regard to Example IV no significant difference was observed between the permeation of MN through skin samples treated with neat or thirty percent by weight of an organosilicon compound similar to the cyclic polydimethylsiloxanes described in the Japanese Kokai Patent 58-128324 when compared to control values.

In contrast, the organosilicon compounds of the present invention were shown to enhance the flux of the model permeants metronidazole and methyl nicotinate through human skin in vitro. The compounds interact with model structured lipids and by inference lipids in the stratum corneum and function as enhancers for metronidazole and methyl nicotinate. The enhancer activity of the organo-silicon compounds of the present invention is believed to be attributable in part to their ability to disrupt the lipid domains in the stratum corneum.

It will be apparent from the foregoing that many other variations and modifications may be made in the compounds, compositions, structures and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A composition comprising:
    a drug capable of delivery to the skin of a human or animal body; and
    a vehicle for delivering the drug, containing an organosilicon compound selected from the group consisting of polysiloxanes having silicon-bonded carboxyalkyl or alkylsulphoxide groups.

2. A composition according to claim 1 wherein the organosilicon compound is of the average general formula $R'_aR_{3-a}SiO[R_2SiO]_m[R'RSiO]_xSiR'_aR_{3-a}$ in which at least one R' represents a carboxyalkyl group —$(CH_2)_yCOOH$ or an alkylsulphoxide group —$(CH_2)_z$-SOR and the remainder are groups R, R represents a monovalent hydrocarbon group having from 1 to 6 carbon atoms, the groups R being at least predominantly methyl, a has a value of 1, y is an integer having a value of one to thirty; z is an integer having a value of one to ten and m and x have values such that the organosilicon compound is a liquid at room temperature.

3. A composition according to claim 2 in which the organo-silicon compound has a formula selected from the group consisting of

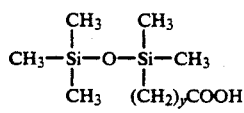

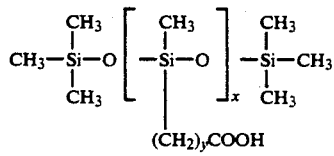

and

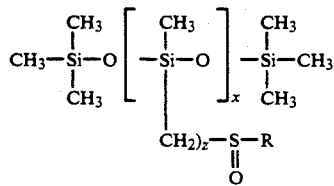

4. A composition according to claim 3 in which the organo-silicon compound has the formula

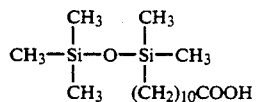

5. A composition according to claim 3 in which the organosilicon compound has the formula

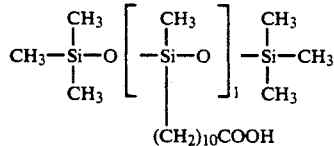

6. A composition according to claim 3 in which the organo-silicon compound has the formula

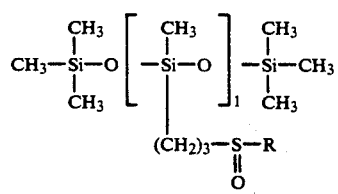

7. A composition according to claim 1 which includes a solvent for the organosilicon compound, the solvent being present in an amount in order to provide a solvent solution containing from three to thirty percent by weight of the organosilicon compound.

8. A composition according to claim 7 in which the solvent is ethanol.

9. A composition according to claim 1 in which the drug is hydrophobic.

10. A composition according to claim 1 in which the drug is hydrophilic.

11. A composition according to claim 1 in which the drug is metronidazole.

12. A composition according to claim 1 in which the drug is methyl nicotinate.

13. A method of delivering an active agent to the skin of a human or animal body comprising the steps of:
   (a) providing the composition of claim 1; and
   (b) applying the composition of (a) topically to the skin of the body, wherein permeation of the drug transdermally is accelerated.

14. The method of claim 13 in which the organosilicon compound of step (a) has a formula selected from the group consisting of

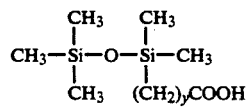

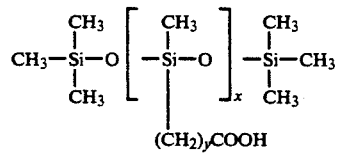

and

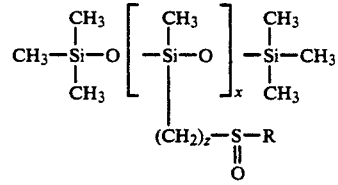

in which x is an integer having a value of one to about one thousand; y is an integer having a value of one to about thirty; z is an integer having a value of one to ten and R is an alkyl radical having from one to six carbon atoms.

15. The method of claim 14 wherein the organosilicon compound of step (a) is applied according to step (b) to the skin in the form of a solvent solution containing from three to thirty percent by weight of the organosilicon compound.

16. The method of claim 13 in which the drug is metronidazole.

17. The method of claim 13 in which the drug is methyl nicotinate.

18. The method of claim 13 in which step (b) further comprises applying the organosilicon compound of step (a) to the skin prior to and independently of the application of the drug to the skin.

19. The method of claim 15 in which the drug is hydrophobic.

20. The method of claim 15 in which the drug is hydrophilic.

21. The method of claim 15 in which the solvent is ethanol.

* * * * *